United States Patent [19]

Diamond et al.

[11] 4,362,671

[45] Dec. 7, 1982

[54] SELECTIVE HYDROGENATION OF DINITRILE TO OMEGA-AMINONITRILE CATALYZED BY RHODIUM ORGANONITROGEN COMPLEX CATALYST

[75] Inventors: Steven E. Diamond, New Providence; Frank Mares, Whippany, both of N.J.; Andrew Szalkiewicz, New York, N.Y.

[73] Assignee: Allied Corporation, Morris Township, Morris County, N.J.

[21] Appl. No.: 314,635

[22] Filed: Oct. 26, 1981

[51] Int. Cl.³ ............... C07C 120/00; C07C 121/43
[52] U.S. Cl. ............................................ 260/465.5 R
[58] Field of Search ............... 564/490, 491, 492; 260/465.5 R

[56] References Cited

U.S. PATENT DOCUMENTS

| | | | |
|---|---|---|---|
| 2,208,598 | 7/1940 | Rigby | 260/465.5 R |
| 2,257,814 | 10/1941 | Rigby | 260/465.5 R |
| 2,762,835 | 9/1956 | Swerdloff | 260/465.5 R |
| 4,313,018 | 1/1982 | Holy et al. | 564/490 X |

OTHER PUBLICATIONS

Mestroni, et al., Journal of Organometallic Chemistry 140, (1977), pp. 63-72.
Cramer, J. A. C. S., (1964), 86, pp. 217-222.
Jacobson, et al., J. A. C. S., (1979), 101, pp. 6938-6946.
Card, et al., Inorganic Chemistry, 17, (1978), pp. 2345-2349.

Primary Examiner—Joseph Paul Brust
Attorney, Agent, or Firm—Alan M. Doernberg; Gerhard H. Fuchs

[57] ABSTRACT

A dinitrile is reacted with hydrogen in the presence of a solvent and a catalyst to form an omega-aminonitrile such as epsilon-aminocapronitrile at high selectivity. The catalyst is a rhodium complex of the formula (RR'Rh)A reacted with a strong base such as sodium hydroxide. R is derived from a diene such as 1,5-hexadiene. R' is a heterocyclic containing an aromatic ring nitrogen. A is a complex monovalent anion such as hexafluorophosphate.

11 Claims, No Drawings

SELECTIVE HYDROGENATION OF DINITRILE TO OMEGA-AMINONITRILE CATALYZED BY RHODIUM ORGANONITROGEN COMPLEX CATALYST

DESCRIPTION

BACKGROUND OF THE INVENTION

The present invention relates to the selective hydrogenation of nitriles such as adiponitrile to omega-aminonitriles such as epsilon-aminocapronitrile, employing a Group VIII metal-containing catalyst.

Group VIII noble metals are well known catalysts for various hydrogenations of organic compounds. One such hydrogenation is the complete hydrogenation of adiponitrile to hexamethylenediamine by a platinum or palladium catalyst. While the diamine product is widely used for producing diacid-diamine-type polyamides such as Nylon 66, it would be desirable to also produce from the dinitrile the partial hydrogenation product, epsilon-aminocapronitrile, since this compound could be cyclized into caprolactam and polymerized to produce Nylon-6. While some attempts have been made with certain Group VIII metals or complexes to achieve selective hydrogenation, a process with high selectivity to epsilon-aminocapronitrile, or other omega-aminonitriles, at moderate conversion and with a catalyst which can be easily handled and conveniently recycled have not yet been found.

Rhodium complexes have found few practical applications in hydrogenations. We recently proposed certain rhodium complexes for hydrogenation of anthraquinones as part of a cyclic process to produce hydrogen peroxide in our copending application, U.S. Ser. No. 244,844, filed Mar. 18, 1981 now U.S. Pat. No. 4,336,241. Other rhodium or rhodium-containing catalyzed hydrogenations are disclosed in Paul N. Rylander, *Catalytic Hydrogenation In Organic Syntheses* (N.Y. 1979) and Brian R. James, *Homogeneous Hydrogenation* (N.Y. 1973). Rhodium-based catalysts have not, however, been known to selectively hydrogenate dinitriles to aminonitriles.

BRIEF DESCRIPTION OF THE INVENTION

It has been discovered that a class of rhodium complexes, containing as one ligand certain organonitrogen materials, can be used to selectively hydrogenate dinitriles to omega-aminonitriles. Accordingly, the present invention includes a process for selectively producing an omega-aminonitrile which comprises reacting at a temperature of between about ambient (e.g. 20° C.) and about 200° C. a dinitrile of the formula $N\equiv C-(CH_2)_n-C\equiv N$ with n being an integer from 1 to 10 with hydrogen at a partial pressure of at least about 1 atmosphere in the presence of:

(a) a solvent, and (b) a rhodium-containing catalyst prepared by reacting with a strong hydroxide base and then hydrogenating a rhodium complex of the formula (RR'Rh)A wherein R is derived from a non-allenic hydrocarbon diene of at least 4 carbons, R' is an aromatic heterocyclic with at least one aromatic ring nitrogen and only C, N and H and A is a complex anion which serves as a counteranion for the cation RR'Rh with rhodium being at valence +1;

and recovering the omega-aminonitrile of the formula $N\equiv C-(CH_2)_n-CH_2-NH_2$ as the major product.

DETAILED DESCRIPTION OF THE INVENTION

The dinitrile used as reactant in the present process may be adiponitrile (wherein n is 4 in the above formula) or may be other similar dinitriles of 3–12 carbons, such that n can vary from 1 to 10. Adiponitrile is most preferred, with somewhat less preferred drinitriles including malononitrile, succinnonitrile, glutaronitrile and pimelonitrile.

The dinitrile is present in the reaction mixture dissolved in a solvent such as an acyclic or cyclic ether. The preferred solvent is a 1:1 mixture of tetrahydrofuran and methanol, with other suitable solvents including ethanol, dioxane and diglyme. The amount of solvent is not critical, but should be at least that sufficient to dissolve the dinitrile and base, and preferably dissolve some hydrogen.

Hydrogen is normally present as a gas at low to moderate pressure in contact with the solution of dinitrile, with some hydrogen dissolved in the solvent. Partial pressures of hydrogen of at least about one atmosphere, and preferably between about 5 and 100 atmospheres are preferred. The hydrogen pressure correlates somewhat with the reaction temperature, which is suitably between about 20° C. and about 200° C., and is preferably between about 20° C. and about 100° C. The total operating pressure is generally equal to or only slightly above the pressure of hydrogen, with other gaseous materials present generally being limited.

The rhodium complex used to prepare the catalyst of the present process can be described by the formula (RR'Rh)A. The first ligand, R, is that derived from a diene such as 1,5-hexadiene. Other suitable dienes from which the ligand R can originate include norbornadiene and 1,5-cyclooctadiene. In addition to such non-conjugated dienes, conjugated dienes such as 1,3-butadiene and 2,4-hexadiene may also be used. Preferred dienes are those of 6 to 8 carbons. The ligand derived from 1,5-hexadiene is most preferred.

The ligand R' is derived from a heterocyclic organic compound containing a ring nitrogen. The nitrogen should be bonded to two ring carbons as is the case for the nitrogen in pyridine and both nitrogens in 2,2'-bipyridine. 2,2'-Bipyridine is the preferred monomeric source for the ligand R', with other suitable monomeric sources including 1,10-phenanthroline and methyl substituted phenanthrolines. When the ligand R' is derived from a monomeric source, both the rhodium complex and the resultant catalyst are preferably soluble in the solvent, such that the catalyst operates as a homogeneous catalyst. In some modes of the invention, however, the ligand R' is derived from a polymeric structure containing as a pendant group the heterocyclic moiety. Such structures may be achieved by bonding certain heterocyclic compounds or their derivatives onto an inert polymeric backbone, as in the case of bonding 2,2'-bipyridine moieties to the phenyl rings of polystyrene. Within this group of catalysts, ligands R' derived from 2,2'-bipyridine bonded to an inert support are preferred, with polystyrene and especially polystyrene beads being the preferred support.

The counteranion for the rhodium-containing complex cation is designated in the above formula by the symbol A. "A" may be any anion which is inert under the reaction conditions, and is preferably a fluorine-containing anion such as hexafluorophosphate and tetrafluoroborate. The preferred complex anion A is the hexafluorophosphate anion. Other somewhat less preferred anions include tetraphenylborate, chloride and bromide. The anion should be present in an amount sufficient to provide electric neutrality to the complex, with rhodium being at valence state +1. Since ligands R and R' are generally electrically neutral, the rhodium, while having four ligands, generally has a charge of only +1 which thus becomes the charge of RR'Rh.

The formation of the active catalyst from the above rhodium catalyst occurs in two steps. First reaction with a strong base, which is preferably an alkali metal hydroxide such as sodium hydroxide, preferably in an aliphatic alcohol such as methanol with an equal amount of an aprotic solvent, preferably tetrahydrofuran. The base reaction should be conducted with at least an equivalent amount of base compared to rhodium complex. Thereafter, the basic complex should be hydrogenated to form the active catalyst. It is contemplated that the hydrogenation may take place either as a pretreatment, prior to introduction of dinitrile, or in situ. It is preferred for most of the present catalysts that the hydrogenation be conducted as a pretreatment.

The presence of alkali metal hydroxide suppresses the formation of certain by-products, and especially the cyclic secondary amine (e.g. azacycloheptane), and the linear secondary amine (e.g. di(5-cyanopentyl)amine), both of which are formed by condensation of an imine intermediate with an amine which may be present at the other end of the same molecule or on a different molecule of omega-aminonitrile.

The present invention is illustrated by the following examples which are not intended to limit the invention.

EXAMPLE 1

The rhodium containing catalyst (2,2'-bipyridine)(1,5-hexadiene)rhodium hexafluorophosphate was prepared in accordance with a known method as described in the *Journal of Organometallic Chemistry* of 1977, volume 140, pages 63–72 at page 70. 160.6 mg of this complex and 251.2 mg of sodium hydroxide were dissolved in a 1:1 mixture of methanol and tetrahydrofuran (20 mL). Hydrogen gas was bubbled through the solution for 30 minutes. Concurrently, hydrogen gas was bubbled through approximately 3 mL of adiponitrile. At this time both the catalyst mixture and the adiponitrile were loaded into a stainless steel autoclave under an argon atmosphere. The autoclave was pressured to approximately 250 psi (1724 kPa) with hydrogen and heated for approximately 2 hours at 100° C. with constant stirring. At this time the autoclave was vented and opened. The liquid was analyzed by standard gas chromatographic techniques to yield epsilon-aminocapronitrile as the major product. The conversion of adiponitrile was 77% with a selectivity to epsilon-aminocapronitrile of 73%. The ratio of epsilon-aminocapronitrile to 1,6-hexanediamine was approximately 22.

EXAMPLE 2

Example 1 was repeated with 154.5 mg of rhodium catalyst and 256.9 mg of sodium hydroxide at room temperature. After approximately 2 hours the reaction was stopped and analyzed. The conversion of adiponitrile was 64% with a selectivity to epsilon-aminocapronitrile of 84%. The ratio of epsilon-aminocapronitrile to 1,6-hexanediamine was approximately 16.

EXAMPLE 3

Example 1 was repeated with 158.2 mg of rhodium catalyst and 72.7 mg of sodium hydroxide at room temperature. After approximately 5 hours the reaction was stopped and analyzed. The conversion of adiponitrile was 77% with a selectivity to epsilon-aminocapronitrile of 52%. The ratio of epsilon-aminocapronitrile to 1,6-hexanediamine was approximately 32. A large amount of the secondary amine di(5-cyanopentyl)amine was also present. This example demonstrates the deliterious effect reductions of the amount of alkali metal hydroxide have on selectivity.

COMPARATIVE EXAMPLE 4

Example 1 was repeated with 156.0 mg of rhodium catalyst leaving out the alkali metal hydroxide. The reaction was carried out at room temperature for approximately 4 hours followed by heating to 50° C. for approximately 10 hours. At this time analysis of the reaction mixture showed that no reaction had taken place. The adiponitrile was recovered unchanged.

EXAMPLE 5

Example 1 was repeated with 474.1 mg of rhodium catalyst, 737.5 mg of sodium hydroxide, 60 mL of a 1:1 mixture of methanol and tetrahydrofuran and approximately 10 mL of adiponitrile. In this case the pressure of hydrogen was approximately 1700 psi (11721 kPa). After approximately 2 hours of reaction at room temperature the reaction was analyzed. Almost complete conversion of the adiponitrile was found (98%). The selectivity to epsilon-aminocapronitrile was 60% with its ratio to 1,6-hexanediamine at approximately 2.5.

EXAMPLE 6

Example 1 was repeated with 163.8 mg of rhodium catalyst and 2125.6 mg of a strong anion exchange resin chiefly in the basic form in place of the alkali metal hydroxide. The reaction was carried out for approximately 4 hours at room temperature at which time the mixture was analyzed. The conversion of adiponitrile was 41% with a selectivity to epsilon-aminocapronitrile of 68%. The ratio of epsilon-aminocapronitrile to 1,6-hexanediamine was very high. A large amount of the secondary amine di(5-cyclopentyl)amine was also present.

EXAMPLE 7

Hexadiene rhodium chloride dimer complex of formula $(CH_2=CHCH_2CH_2CH=CH_2RhCl)_2$ was prepared by the method in the *Journal of the American Chemical Society* of 1964, volume 86, pages 217–222 at page 221. Polystyrene was brominated as described in the *Journal of the American Chemical Society* of 1979, volume 101, pages 6938–6946 at page 6945. This polymer was then functionalized with bipyridine by a procedure as in *Inorganic Chemistry* of 1978, volume 17, pages 2345–2349 at page 2348. Analysis showed C-84.61%, H-7.24%, N-1.87%, i.e. a molecular weight of 1,497 per 2,2'-bipyridine group. The functionalized chloride polymer beads (4.95 g) and the hexadiene rhodium complex (2.20 g) were then added to degassed tetrahydrofuran (mole ratio of 3:1, rhodium complex:bipyridyl groups) and the reaction mixture was degassed under argon while stirring for 2 hours. The solution became dark brown. Ammonium hexafluorophosphate (1.75 g) was added and stirring was continued for 30 minutes. The reaction mixture was filtered and the precipitate was washed with tetrahydrofuran, water, toluene and ethyl acetate. 405.4 mg of this polymer bound catalyst and 242.3 mg of sodium hydroxide were added to 20 mL of a 1:1 mixture of methanol and tetrahydrofuran. Hydrogen gas was bubbled through this suspension for 30 minutes. Concurrently, hydrogen gas was bubbled through approximately 3 mL of adiponitrile. At this time both the catalyst mixture and the adiponitrile were loaded into the stainless steel autoclave under an argon atmosphere. The autoclave was pressurized to approximately 250 psi (1724 kPa) with hydrogen and stirred at room temperature for approximately 20 hours. At this time the autoclave was vented, opened, and the polymer bound catalyst filtered. It was washed with ether and dried in a vacuum desiccator. The reaction filtrate was analyzed by the usual gas chromotographic techniques to yield epsilon-aminocapronitrile as the major product. The conversion of adiponitrile was 85% with a selectivity to epsilon-aminocapronitrile of 62%. The ratio of epsilon-aminocapronitrile to 1,6-hexanediamine was approximately 10. A large amount of the secondary amine di(5-cyanopentyl)amine was also present.

EXAMPLE 8

Example 7 was repeated with the used catalyst from example 7 and no additional sodium hydroxide. After approximately 20 hours at room temperature the reaction mixture was analyzed to yield a 55% conversion of adiponitrile with a selectivity to epsilon-aminocapronitrile of 38%. The ratio of epsilon-aminocapronitrile to 1,6-hexanediamine was very high. A large amount of the secondary amine di(5-cyanopentyl) amine was also present.

What is claimed is:

1. A process for selectively producing an omega-aminonitrile which comprises reacting at a temperature of between about 20° C. and about 200° C. a dinitrile of the formula $N \equiv C-(CH_2)_n-C \equiv N$ with n being an integer from 1 to 10 with hydrogen at a partial pressure of at least about one atmosphere in the presence of:

(a) a solvent, and
(b) a rhodium-containing catalyst prepared by reacting with a strong hydroxide base and then hydrogenating a rhodium complex of the formula (RR′Rh)A wherein R is derived from a non-allenic hydrocarbon diene of at least 4 carbons, R′ is an aromatic heterocyclic with at least one aromatic ring nitrogen and only C, N and H and A is a complex monovalent anion which serves as a counteranion for the cation RR′Rh with rhodium being at valence +1;

and recovering the omega-aminonitrile of the formula $N \equiv C\text{-}(CH_2)_n-CH_2-NH_2$ as the major product.

2. The process of claim 1 wherein said solvent is a mixture of tetrahydrofuran and methanol.

3. The process of claim 1 wherein said strong hydroxide base is an alkali metal hydroxide.

4. The process of claim 3 wherein said alkali metal hydroxide is sodium hydroxide.

5. The process of claim 1 wherein R is derived from 1,5-hexadiene.

6. The process of claim 1 wherein R′ is derived from 2,2′-bipyridine.

7. The process of claim 1 wherein R′ is derived from 2,2′-bipyridine supported on an inert support.

8. The process of claim 7 wherein said inert support is polystyrene.

9. The process of claim 1 wherein A is hexafluorophosphate.

10. The process of claim 1 wherein A is tetrafluoroborate.

11. The process of claim 1 or 2 or 3 or 4 or 5 or 6 or 7 or 8 or 9 or 10 wherein n is 4.

* * * * *